US008588905B2

(12) United States Patent  (10) Patent No.: US 8,588,905 B2
Williamson  (45) Date of Patent: Nov. 19, 2013

(54) METHOD AND SYSTEM FOR ADJUSTING A STIMULATION RATE OF AN IMPLANTABLE MEDICAL DEVICE

(75) Inventor: Richard Williamson, Santa Monica, CA (US)

(73) Assignee: Pacesetter, Inc., Sylmar, CA (US)

( * ) Notice: Subject to any disclaimer, the term of this patent is extended or adjusted under 35 U.S.C. 154(b) by 632 days.

(21) Appl. No.: 12/790,056

(22) Filed: May 28, 2010

(65) Prior Publication Data
US 2011/0295334 A1  Dec. 1, 2011

(51) Int. Cl.
*A61N 1/362* (2006.01)

(52) U.S. Cl.
USPC ................................. 607/9; 607/25

(58) Field of Classification Search
USPC .......................... 607/9, 25, 26, 27
See application file for complete search history.

(56) References Cited

U.S. PATENT DOCUMENTS

| 5,749,906 | A * | 5/1998 | Kieval et al. ................ 607/9 |
| 6,615,089 | B1 | 9/2003 | Russie et al. |
| 6,928,326 | B1 | 8/2005 | Levine |
| 6,950,704 | B1 | 9/2005 | Bradley |
| 6,963,775 | B2 | 11/2005 | Russie et al. |
| 6,973,350 | B1 | 12/2005 | Levine et al. |
| 7,006,869 | B2 | 2/2006 | Bradley |
| 7,035,687 | B1 | 4/2006 | Levine et al. |
| 7,187,972 | B1 | 3/2007 | Fain et al. |
| 7,286,876 | B2 | 10/2007 | Yonce et al. |
| 7,412,287 | B2 | 8/2008 | Yonce et al. |
| 2002/0193835 | A1 * | 12/2002 | Baker ................... 607/9 |
| 2003/0069611 | A1 * | 4/2003 | Levine ................ 607/27 |
| 2004/0148109 | A1 | 7/2004 | Fischer |
| 2006/0149328 | A1 | 7/2006 | Parikh et al. |
| 2006/0224193 | A1 | 10/2006 | Hess |

FOREIGN PATENT DOCUMENTS

WO  2006069032 A1  6/2006
WO  2007073514 A1  6/2007

OTHER PUBLICATIONS

Kam, Ruth MBBS, "Automatic Capture Verification in Pacemakers (Autocapture)—Utility and Problems," Indian Pacing Electrophysiol J. Apr.-Jun. 2004;4(2):73-78.

* cited by examiner

*Primary Examiner* — Joseph Dietrich

(57) ABSTRACT

An implantable medical device includes a lead, a pulse generator, a cardiac signal module, a fusion detection module and a rate modification module. The lead includes electrodes that are configured to be positioned within a heart to sense cardiac signals of the heart. The pulse generator delivers stimulus pulses to the heart through at least one of the electrodes. The cardiac signal module monitors the cardiac signals and directs the pulse generator to deliver one or more of the stimulus pulses to the heart at a stimulation rate based on the cardiac signals. The fusion detection module identifies a presence of fusion-based behavior of the heart that is associated with delivery of the one or more of the stimulus pulses. The rate modification module then adjusts the stimulation rate based on the presence of the fusion-based behavior.

20 Claims, 8 Drawing Sheets

METHOD AND SYSTEM FOR ADJUSTING A STIMULATION RATE OF AN IMPLANTABLE MEDICAL DEVICE

FIELD OF THE INVENTION

Embodiments of the present invention generally pertain to implantable medical devices and more particularly to methods and systems that adjust a stimulation rate at which stimulus pulses are supplied to a heart.

BACKGROUND OF THE INVENTION

An implantable medical device (IMD) is implanted in a patient to monitor, among other things, electrical activity of a heart and to deliver appropriate electrical therapy, as required. Implantable medical devices include pacemakers, cardioverters, defibrillators, implantable cardioverter defibrillators (ICD), and the like. The electrical therapy produced by an IMD may include pacing pulses, cardioverting pulses, and/or defibrillator pulses to reverse arrhythmias (e.g., tachycardias and bradycardias) or to stimulate the contraction of cardiac tissue (e.g., cardiac pacing) to return the heart to its normal sinus rhythm. These pulses are referred to as stimulus or stimulation pulses.

Some IMDs supply a pacing therapy to hearts to treat ventricular tachycardia and/or ventricular fibrillation. The pacing therapy may include supplying stimulus pulses to the left and right ventricles of the heart at a stimulation rate. Applying the stimulus pulses to the ventricles may restore mechanical synchrony to the heart. For example, the stimulus pulses may return the heart to a normal rate of ventricular contraction.

Pacing therapies of some known IMDs monitor cardiac signals of the heart to determine when to supply stimulus pulses. For example, after detecting a paced or intrinsic cardiac event, such as a ventricular contraction, the IMD continues to monitor the cardiac signals to determine if a subsequent intrinsic cardiac event occurs during a predetermined escape interval after the preceding cardiac event. If no subsequent cardiac event is detected during the predetermined escape interval, then the IMD supplies a stimulus pulse to the heart to induce contraction of the heart.

During ventricular tachycardia or ventricular fibrillation, intrinsic ventricular contractions may not provide the same level of cardiac output as paced ventricular contractions, or ventricular contractions that are induced by the delivery of stimulus pulses to one or more of the ventricles. For example, intrinsic ventricular contractions may pump less blood through the heart when compared to paced ventricular contractions during ventricular tachycardia or ventricular fibrillation.

Some known IMDs increase the stimulation rate at which stimulus pulses are applied to the heart to increase the number of paced contractions and decrease the number of intrinsic contractions. The IMDs monitor intrinsic and paced ventricular contractions during ventricular tachycardia and ventricular fibrillation in order to determine the stimulation rate. The IMDs determine the stimulation rate based on the predetermined escape interval. For example, the IMDs may decrease the escape interval of a ventricle for subsequent cardiac cycles when an intrinsic ventricular contraction is sensed during the escape interval of a current cardiac cycle. The escape interval is decreased to increase the possibility that the escape interval expires and the IMD delivers a stimulus pulse prior to intrinsic ventricular contraction. For example, decreasing the escape interval provides a shorter time in which an intrinsic contraction must occur before the IMD delivers a stimulus pulse to the heart. On the other hand, an IMD may increase the escape interval if the IMD has been pacing the heart for at least a predetermined time period. The IMD increases the escape interval to reduce the stimulation rate and avoid pacing the heart at an accelerated rate for greater than the predetermined time period.

The known IMDs described above do not, however, account for the presence of fusion-based behavior of the heart. Fusion-based behavior of the heart may reduce the cardiac output of the heart. Reducing the cardiac output of the heart during a pacing therapy may prolong the therapy or fail to remedy the ventricular tachycardia or ventricular fibrillation. Fusion-based behavior may include fusion and pseudo-fusion between paced and intrinsic cardiac events. Fusion may occur when a stimulus pulse is applied to a heart chamber at approximately the same time that an intrinsic contraction of the heart chamber begins. Pseudo-fusion may occur when a stimulus pulse is applied to the heart chamber shortly after an intrinsic contraction of the heart chamber begins. By failing to account for the presence of fusion-based behavior while pacing the heart, some known IMDs continue to ineffectively pace the heart.

BRIEF SUMMARY OF THE INVENTION

In one embodiment, an implantable medical device is provided. The device includes a lead, a pulse generator, a cardiac signal module, a fusion detection module and a rate modification module. The lead includes electrodes that are configured to be positioned within a heart to sense cardiac signals of the heart. The pulse generator delivers stimulus pulses to the heart through at least one of the electrodes. The cardiac signal module monitors the cardiac signals and directs the pulse generator to deliver one or more of the stimulus pulses to the heart at a stimulation rate based on the cardiac signals. The fusion detection module identifies a presence of fusion-based behavior of the heart that is associated with delivery of the one or more of the stimulus pulses. The rate modification module then adjusts the stimulation rate based on the presence of the fusion-based behavior.

In another embodiment, a method for adjusting a stimulation rate at which an implantable medical device applies stimulus pulses to a heart is provided. The method includes monitoring cardiac signals of the heart and delivering one or more stimulus pulses to the heart at the stimulation rate based on the cardiac signals. The method also includes identifying a presence of fusion-based behavior of the heart that is associated with delivery of the one or more of the stimulus pulses and adjusting the stimulation rate based on the presence of the fusion-based behavior.

In another embodiment, a computer readable storage medium for use in an implantable medical device having a lead including electrodes configured to be positioned within a heart, a pulse generator to deliver stimulus pulses to the heart, and a microcontroller is provided. The computer readable storage medium includes instructions to direct the microcontroller to monitor cardiac signals of the heart using one or more of the electrodes and to instruct the pulse generator to deliver one or more stimulus pulses to the heart at a stimulation rate using at least one of the electrodes when consecutive cardiac events occur outside of an escape interval. The instructions also direct the microcontroller to identify a presence of fusion-based behavior of the heart that is associated with delivery of the one or more of the stimulus pulses and to adjust the stimulation rate based on the presence of the fusion-based behavior.

BRIEF DESCRIPTION OF THE DRAWINGS

The drawings illustrate generally, by way of example, but not by way of limitation, various embodiments discussed in the present document.

DETAILED DESCRIPTION OF THE INVENTION

In the following detailed description, reference is made to the accompanying drawings which form a part hereof, and in which are shown by way of illustration specific embodiments in which the present invention may be practiced. These embodiments, which are also referred to herein as "examples," are described in sufficient detail to enable those skilled in the art to practice the invention. It is to be understood that the embodiments may be combined or that other embodiments may be utilized, and that structural, logical, and electrical variations may be made without departing from the scope of the present invention. The following detailed description is, therefore, not to be taken in a limiting sense, and the scope of the present invention is defined by the appended claims and their equivalents. In this document, the terms "a" or "an" are used, as is common in patent documents, to include one or more than one. In this document, the term "or" is used to refer to a nonexclusive or, unless otherwise indicated.

In accordance with certain embodiments, methods and systems are provided for adjusting a stimulation rate at which stimulus pulses are applied to a heart. The stimulation rate may be adjusted based on the presence of fusion-based behavior that is identified in the heart after delivery of one or more of the stimulus pulses to the heart.

Figure 1:
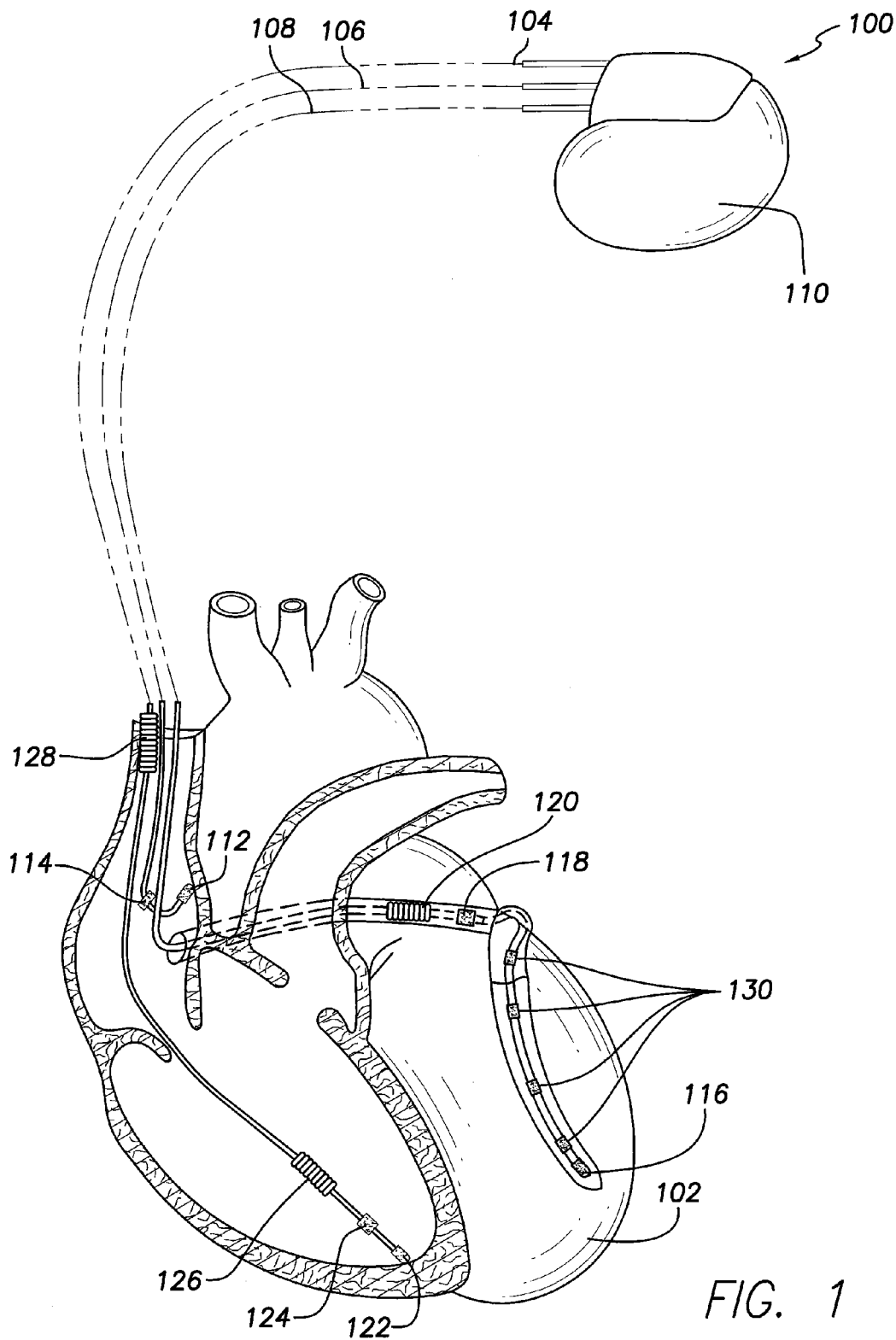
FIG. 1 illustrates an implantable medical device (IMD) coupled to a heart in accordance with one embodiment.

FIG. 1 illustrates an implantable medical device (IMD) 100 coupled to a heart 102 in accordance with one embodiment. The IMD 100 may be a cardiac resynchronization therapy (CRT) pacemaker. Alternatively, the IMD 100 may be a cardiac pacemaker, an ICD, a defibrillator, an ICD coupled with a pacemaker, a cardiac resynchronization therapy defibrillator (CRT-D), and the like. The IMD 100 includes a housing 110 that is joined to several leads 104, 106, 108. The leads 104, 106, 108 are located at various locations of the heart 102, such as an atrium, a ventricle, or both, to measure cardiac signals of the heart 102 and to deliver stimulus pulses, such as pacing pulses. The leads 104, 106, 108 include the right ventricular (RV) lead 104, the right atrial (RA) lead 106, and the coronary sinus lead 108. Several electrodes are coupled with the leads 104, 106, 108 for sensing cardiac signals and/or for delivering stimulus or stimulation pulses to the heart 102. The housing 110 may be one of the electrodes and may be referred to as the "can", "case", or "case electrode."

The RV lead 104 is coupled with an RV tip electrode 122, an RV ring electrode 124, and an RV coil electrode 126. The RV lead 104 may include a superior vena cava (SVC) coil electrode 128. The right atrial lead 106 includes an atrial tip electrode 112 and an atrial ring electrode 114. The coronary sinus lead 108 includes a left ventricular (LV) tip electrode 116, one or more left atrial (LA) ring electrodes 118 and an LA coil electrode 120. Alternatively, the coronary sinus lead 108 may be a quadropole lead that includes several electrodes 130 disposed within the left ventricle and along the lead 108 between the LV tip electrode 116 and the LA ring electrode 118. Leads and electrodes other than those shown in FIG. 1 may be included in the IMD 100 and positioned in or proximate to the heart 102.

The IMD 100 monitors cardiac signals of the heart 102 to determine if and when to deliver stimulus pulses to one or more chambers of the heart 102. The IMD 100 may deliver pacing stimulus pulses to pace the heart 102 and maintain a desired heart rate and/or shocking stimulus pulses to treat an abnormal heart rate. The stimulus pulses can be applied to the left and/or right ventricles of the heart 102 to treat ventricular tachycardia and/or ventricular fibrillation, for example. For example, if the IMD 100 senses activity in a chamber of the heart 102 but does not sense additional activity in the chamber within a predetermined time period or window, the IMD 100 may apply a stimulus pulse to the chamber to cause polarization or contraction of the chamber.

Figure 2:
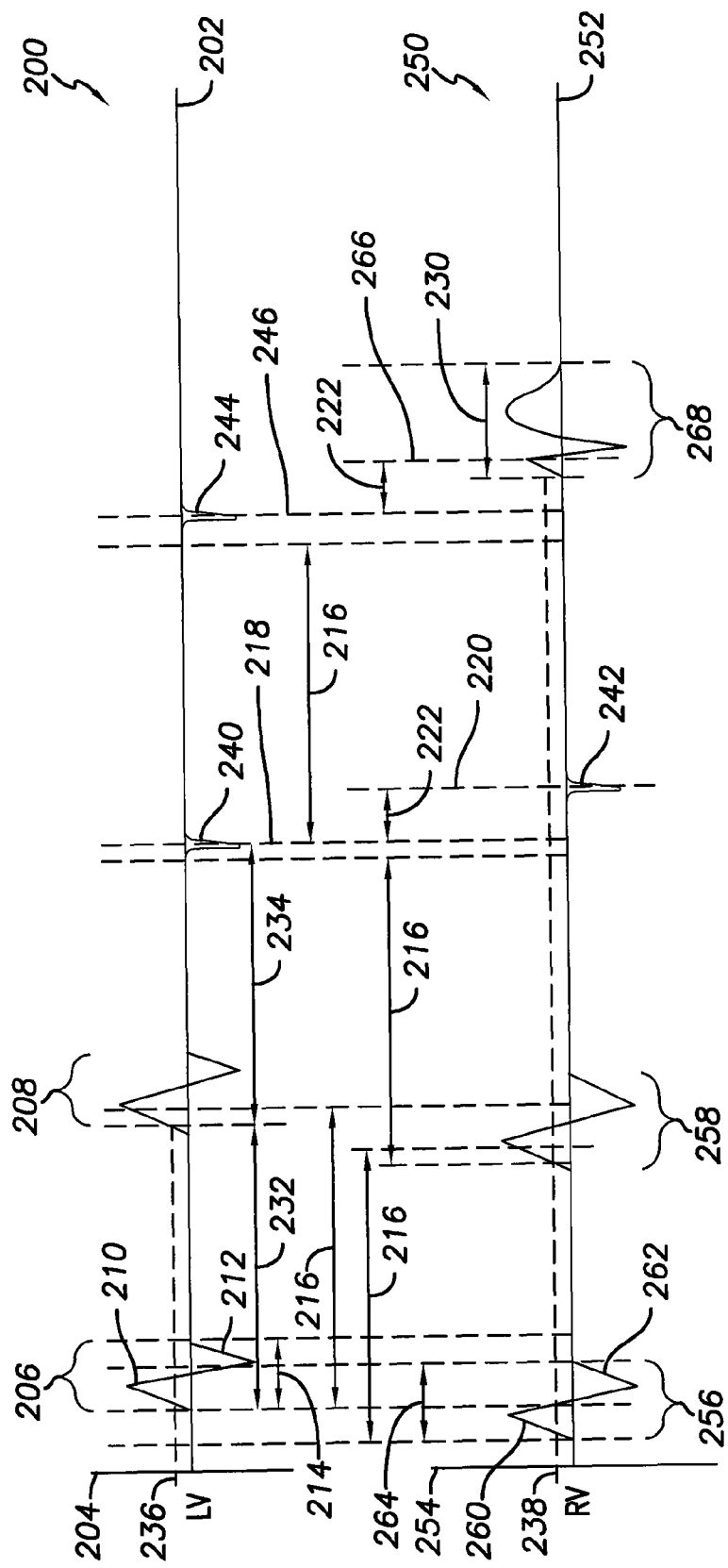
FIG. 2 illustrates an example of a cardiac signal of the heart that is sensed by the IMD shown in FIG. 1.

FIG. 2 illustrates an example of cardiac signals 200, 250 of the heart 102 (shown in FIG. 1) that are sensed by the IMD 100 (shown in FIG. 1). The cardiac signal 200 represents cardiac activity of the left ventricle of the heart 102 while the cardiac signal 250 represents cardiac activity of the right ventricle of the heart 102. The cardiac signals 200, 250 are shown alongside horizontal axes 202, 252 that are representative of time and vertical axes 204, 254 that are representative of the strength or magnitude of the cardiac signals 200, 250. The cardiac signals 200, 250 may be offset above or below the horizontal axes 202, 252.

The cardiac signals 200, 250 include R-waves 206, 256 that correspond to intrinsic ventricular activity. For example, the R-wave 206 may represent intrinsic ventricular contraction of the left ventricle while the R-wave 256 represents intrinsic ventricular contraction of the right ventricle. The R-waves 206, 256 may represent cardiac activity that is not caused by application of a stimulus pulse. Alternatively, the R-waves 206, 256 may represent activity of a different chamber of the heart 102 (shown in FIG. 1). The waveforms of the R-waves 206, 256 include positive deflection portions 210, 260 followed by negative deflection portions 212, 262. The R-waves 206, 256 occur over a time period referred to as an electrical depolarization time 214, 264. The electrical depolarization time 214 of the R-wave 206 includes both the positive and negative deflection portions 210, 212 and the electrical depolarization time 264 includes both the positive and negative deflection portions 260, 262 of the R-wave 256. The electrical depolarization times 214, 264 represent the time period or window over which the left and right ventricles electrically depolarize. While the electrical depolarization times 214, 264 may vary among patients, in general, each of the electrical depolarization times 214, 264 is approximately 75 milliseconds. For example, the electrical depolarization times 214, 264 may be longer for hearts 102 with conduction problems such as left or right bundle branch block The IMD 100 (shown in FIG. 1) monitors one or more of the cardiac signals 200, 250 to determine if consecutive cardiac events occur within an escape interval 216. The escape interval 216 is a time window or period that commences at the detection of the R-wave 206, 250 and lasts for a predetermined amount of time. In the illustrated embodiment, with respect to the left ventricle, the escape interval 216 is a ventricular escape interval that begins when the R-wave 206 exceeds a predetermined detection threshold 236. With respect to the right ventricle, the escape interval 216 begins when the R-wave 256 exceeds a predetermined detection threshold 238.

The escape interval 216 is used to determine when to apply a stimulus pulse to the heart 102 (shown in FIG. 1). For example, the escape interval 216 may be used to determine if consecutive R-waves occur within the time period defined by the escape interval 216. In the example shown in FIG. 2, with respect to the left ventricle, the escape interval 216 begins with the detection of the R-wave 206. If the IMD 100 (shown in FIG. 1) senses cardiac activity, such as a subsequent left ventricular R-wave 208, within the escape interval 216 following the previous left ventricular R-wave 206, then the IMD 100 does not apply a stimulus pulse to the heart 102. With respect to the right ventricle, the escape interval 216 begins with the detection of the R-wave 256. If the IMD 100 senses cardiac activity, such as a subsequent right ventricular R-wave 258 within the escape interval 216 following the previous right ventricular R-wave 256, then the IMD 100 does not apply a stimulus pulse to the heart 102. Typically, the IMD 100 looks for ventricular activity in one ventricular configuration for ventricular timing. This ventricular configuration could be a right ventricular sensing configuration, such as sensing using the right ventricular RV tip electrode 122 to the right ventricular RV ring electrode 124. Alternatively, the sensing configuration could be a left ventricular sensing configuration, such as sensing using the left ventricular LV tip electrode 116 to the left ventricular ring electrode 130. Following the delivery of the stimulus pulses in the right ventricle and left ventricle, however, independent sensing of the right ventricle and left ventricle, respectively, may occur. It is this sensing following pacing events that may be used to determine fusion, or if fusion-based behavior has occurred, even if the sensing for ventricular timing uses only one configuration for ventricular sensing.

On the other hand, if the escape interval 216 following an R-wave lapses before the IMD 100 (shown in FIG. 1) senses cardiac activity, then the IMD 100 delivers a stimulus pulse to the heart 102 (shown in FIG. 1). With respect to the example shown in FIG. 2, an escape interval 216 that begins with the detection of the subsequent right ventricular R-wave 258 expires without an additional intrinsic cardiac event being sensed by the IMD 100 in the right ventricle. For example, the escape interval 216 expires without an additional subsequent R-wave being detected by the IMD 100 in the right ventricle. As a result, the IMD 100 delivers one or more stimulus pulses to the heart 102. If the IMD 100 is pacing both ventricles of the heart 102, the IMD 100 may deliver an LV stimulus pulse 240 to the left ventricle at a left ventricular pacing time 218 and an RV stimulus pulse 242 to the right ventricle at a right ventricular pacing time 220. The pacing times 218, 220 are separated in time from one another by an interchamber paced delay 222.

The IMD 100 (shown in FIG. 1) continues to monitor cardiac activity of the left and right ventricles for additional cardiac events. The time period between consecutive cardiac events is referred to as an event interval. The event interval begins with the start of a paced or intrinsic cardiac event and terminates with the beginning of the subsequent paced or intrinsic cardiac event. For example, a first event interval 232 begins with detection of the LV R-wave 206 and ends with the detection of the subsequent LV R-wave 208. A second event interval 234 starts with the detection of the subsequent LV R-wave 208 and ends with the application of the LV stimulus pulse 240 at the left ventricular pacing time 218.

The IMD 100 (shown in FIG. 1) determines if additional cardiac activity in either of the left or right ventricles occurs within the escape interval 216 following delivery of a stimulus pulse. For example, the IMD 100 monitors cardiac signals of the left ventricle over the escape interval 216 following the LV stimulus pulse 240 to determine if the left ventricle depolarizes during the escape interval 216. The IMD 100 also may monitor cardiac signals of the right ventricle over the escape interval 216 following the RV stimulus pulse 242 to determine if the right ventricle depolarizes during the escape interval 216.

In the example shown in FIG. 2, the escape interval 216 following the LV stimulus pulse 240 expires without detection of additional activity of the left ventricle. As a result, the IMD 100 delivers another LV stimulus pulse 244 at a left ventricular pacing time 246 and another RV stimulus pulse at a right ventricular pacing time 266. As described above, the LV and RV stimulus pulses are separated in time by the interchamber paced delay 222. In the signals 200, 250 shown in FIG. 2, the previous RV stimulus pulse 242 that was delivered at the right ventricular pacing time 220 causes depolarization of the right ventricle. The paced depolarization of the right ventricle occurs during the same time period or window that the additional RV stimulus pulse is applied at the right ventricular pacing time 266. For example, the paced depolarization of the right ventricle may begin during the interchamber paced delay 222. As a result, the paced depolarization of the right ventricle and the additional RV stimulus pulse that is applied at the pacing time 266 become fused with one another. A fused waveform 268 represents the fusion of the paced depolarization of the right ventricle and the RV stimulus pulse applied at the pacing time 266.

In one embodiment, fusion-based behavior of the heart 102 (shown in FIG. 1) includes the occurrence of one or more of a fusion paced event and a pseudo-fusion paced event. Fusion-based behavior occurs when a stimulus pulse is delivered to the heart 102 by the IMD 100 (shown in FIG. 1) at approximately the same time that an intrinsic cardiac event occurs. For example, a paced fusion event may occur when an intrinsic depolarization or contraction of a chamber of the heart 102 begins at approximately the same time as a stimulus pulse is delivered to the chamber. A paced pseudo-fusion event may occur when a stimulus pulse is delivered to the heart chamber shortly after intrinsic depolarization or contraction of the chamber begins.

The IMD 100 may measure the time period over which the heart 102 depolarizes after application of a stimulus pulse to a ventricle. For example, the time period over which the heart 102 depolarizes after application of the RV stimulus pulse 242 at the right ventricular pacing time 220 may be measured as a paced depolarization time 230. Alternatively, the paced depolarization time 230 may be a predetermined time period stored in a memory accessible by the IMD 100.

In order to avoid fusion-based behavior in the heart 102 (shown in FIG. 1) during abnormal cardiac behavior such as an atrial arrhythmia (e.g., atrial tachycardia or atrial fibrillation) that is conducting into the ventricles intermittently, the IMD 100 (shown in FIG. 1) may adjust the stimulation rate, or the frequency, at which the ventricular stimulus pulses are applied to the heart 102 based on the presence of fusion-based behavior in the heart 102. For example, the IMD 100 may increase the stimulation rate at which stimulus pulses are applied to the ventricles when fusion-based behavior is detected in the heart 102. Alternatively, the IMD 100 may monitor cardiac signals for fusion-based behavior without modifying the stimulation rate. For example, the IMD 100 may apply stimulus pulses during an atrial arrhythmia and monitor the cardiac signals on a beat-by-beat basis to determine if fusion-based behavior is present without adjusting the rate at which the stimulus pulses are supplied. In one embodiment, the IMD 100 adjusts the stimulation rate by modifying the escape interval 216. The stimulation rate may be increased by decreasing the escape interval 216. For example, the escape interval 216 is the period of time over which the IMD 100 monitors cardiac signals of the heart 102 to determine if a cardiac event, such as ventricular contraction, is detected within the escape interval 216, as described above. If the escape interval 216 is decreased, the IMD 100 monitors the cardiac signals of the heart 102 for intrinsic cardiac activity for a shorter period of time before applying stimulus pulses to the heart 102. As the IMD 100 monitors cardiac signals for a shorter period of time before applying stimulus pulses, the stimulus pulses are applied to the heart 102 more rapidly, or at an increased stimulation rate.

Figure 3:
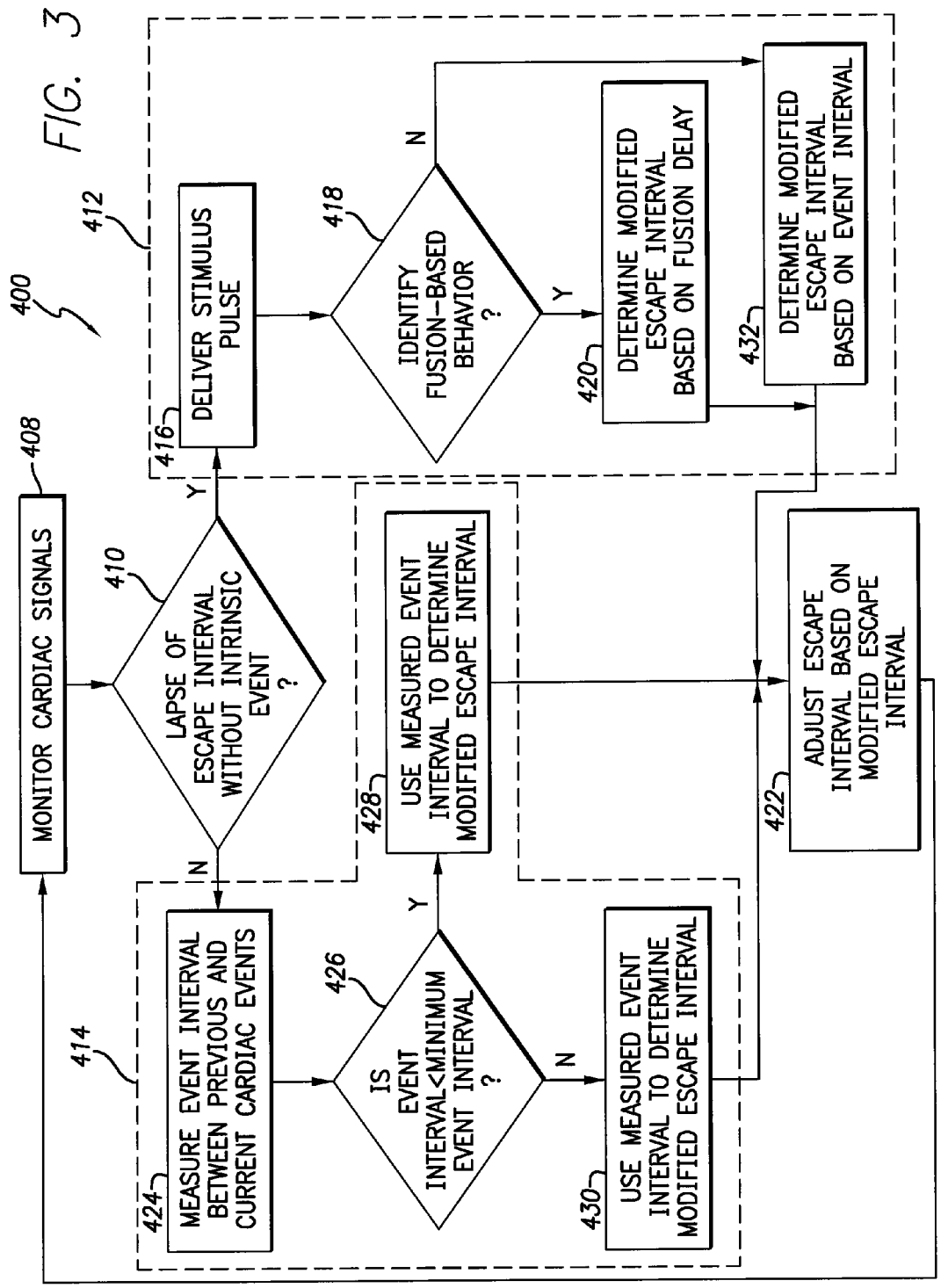
FIG. 3 illustrates a method for adjusting an escape interval of the IMD shown in FIG. 1 according to one embodiment.

FIG. 3 illustrates a method 400 for adjusting a ventricular escape interval of an IMD 100 (shown in FIG. 1) according to one embodiment. At 408, the IMD 100 (shown in FIG. 1) monitors cardiac signals of the ventricles of the heart 102 (shown in FIG. 1). For example, the IMD 100 may monitor cardiac signals representative of ventricular activity of the heart 102 to identify intrinsic ventricular contractions of the heart 102. The cardiac signals also may be monitored to determine the cardiac rate of the heart 102. The cardiac rate is used to determine an escape interval 216 (shown in FIG. 2) of the heart 102 (shown in FIG. 1). As described above, the escape interval 216 is used by the IMD 100 (shown in FIG. 1) to determine whether to supply a stimulus pulse to a chamber of the heart 102. The escape interval 216 may be derived based on the cardiac rate. For example, the escape interval 216 may be measured as the time period extending between consecutive ventricular contractions. The IMD 100 may calculate the escape interval 216 as the time between R-waves 206, 208 (shown in FIG. 2), such as the first event interval 232 (shown in FIG. 2), as described above. Alternatively, a predetermined time period may be used for the escape interval 216. For example, the escape interval 216 may be set to a predetermined value obtained from a memory accessible by the IMD 100.

At 410, after sensing an intrinsic cardiac event, such as an intrinsic ventricular contraction, the IMD 100 continues to monitor the cardiac signals to determine if the escape interval 216 (shown in FIG. 2) lapses without sensing an additional intrinsic cardiac event. For example, the IMD 100 monitors the cardiac signals to determine whether another intrinsic ventricular contraction occurs or begins during the escape interval 216 following the previously sensed ventricular contraction. Flow of the method 400 continues along one of at least two paths 412, 414 depending on whether an additional intrinsic cardiac event is sensed during the escape interval 216. For example, if the escape interval 216 expires before the IMD 100 senses the beginning or presence of an intrinsic cardiac event, then flow of the method 400 continues along a pacing path 412. The escape interval 216 may expire before the IMD 100 senses a subsequent cardiac event when the subsequent cardiac event commences outside of the escape interval 216. On the other hand, if the IMD 100 senses the beginning or occurrence of an intrinsic cardiac event during the escape interval 216, the flow of the method 400 continues along a sensed event path 414.

With respect to the pacing path 412, at 416, a stimulus pulse is delivered to one or more chambers of the heart 102 (shown in FIG. 1). For example, the IMD 100 (shown in FIG. 1) may apply stimulus pulse(s) to one or more of the left and right ventricles of the heart 102. The stimulus pulses are supplied to the heart 102 to induce contraction of the corresponding chambers of the heart 102, as described above. At 418, cardiac signals of the heart 102 (shown in FIG. 1) are examined to determine whether the cardiac signals indicate fusion-based behavior of the heart 102. For example, the IMD 100 (shown in FIG. 1) may monitor cardiac signals after the stimulus pulse(s) are applied to the heart 102 at 416 to identify fusion-based behavior of the heart 102 associated with delivery of the stimulus pulse(s). As described above, fusion-based behavior includes fusion paced events and pseudo-fusion paced events. One or more of several techniques and methods may be used to identify fusion-based behavior of the heart 102. The techniques and methods discussed herein are provided as examples only.

Figure 4:
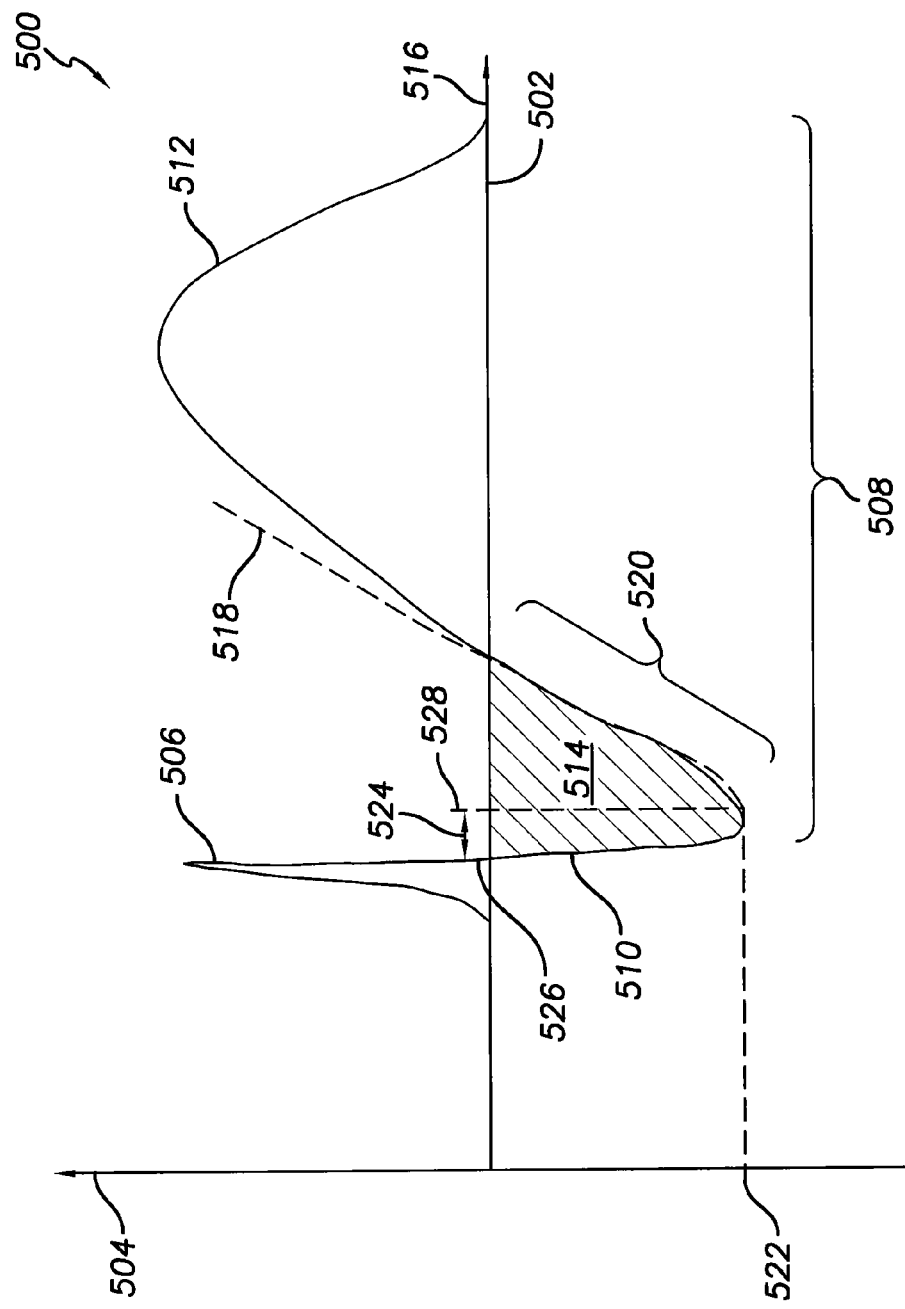
FIG. 4 illustrates a cardiac signal of the heart that is representative of an evoked response of the heart.

With continued reference to the method 400 shown in FIG. 3, FIG. 4 illustrates a cardiac signal 500 of the heart 102 (shown in FIG. 1) representative of an evoked response of the heart 102. The cardiac signal 500 is shown alongside a horizontal axis 502 representative of time and a vertical axis 504 representative of sensed electrical voltage of the heart. In the illustrated embodiment, a baseline 516 of the cardiac signal 500 is coextensive with the horizontal axis 502. Alternatively, the baseline 516 may be biased above or below the horizontal axis 502. The cardiac signal 500 represents an evoked response of the heart 102 to application of a stimulus pulse to one or more chambers of the heart 102. The cardiac signal 500 may be examined at 418 to determine whether the heart 102 is demonstrating fusion-based behavior in response to application of the stimulus pulse applied at 416.

The cardiac signal 500 includes a paced event 506 that is illustrated as a waveform spike. The paced event 506 represents delivery of a stimulus pulse to the heart 102 (shown in FIG. 1) at 416. This pacing spike may or may not be sensed by the activity of the heart 102 as the electronics of delivering the pacing spike may be tuned to prevent the observation of the pacing voltage by the sensing elements of the IMD 100 (shown in FIG. 1). An evoked response waveform 508 follows the paced event 506 and includes a negative portion 510 and a positive portion 512. In one embodiment, the evoked response waveform 508 may be examined at 418 to determine whether the heart 102 is demonstrating fusion-based behavior. One or more of a paced depolarization integral (PDI) 514 and Dmax parameter 518 may be examined at 418 to determine if fusion-based behavior exists. PDI 514 is the area of the negative portion 510 of the evoked response waveform 508. The PDI 514 is represented as the absolute value of the area between the negative portion 510 and the baseline 516 of the cardiac signal 500. The Dmax parameter 518 represents the value of the slope of a positive-sloped section 520 of the evoked response waveform 508 from the negative portion 510 toward the positive portion 512. The positive-sloped section 520 of the evoked response waveform 508 begins subsequent to a low point 522 of the negative portion 510 and extends to the baseline 516 of the evoked response waveform 508. The Dmax parameter 518 is shown as a dashed line in FIG. 4.

In one embodiment, the values of the PDI 514 and the Dmax parameter 518 are measured by the IMD 100 (shown in FIG. 1) and compared to associated thresholds to determine if the heart 102 (shown in FIG. 1) demonstrates fusion-based behavior. The value of the PDI 514 may indicate whether the stimulus pulse applied at 416 resulted in capture in one or more chambers of the heart 102. For example, if the value of the PDI 514 exceeds a predetermined PDI threshold, then the PDI 514 may indicate that capture of the stimulus pulse has occurred. On the other hand, if the value of the PDI 514 does not exceed the predetermined PDI threshold, then the PDI 514 may not indicate that capture has occurred. Additionally, the failure of the PDI 514 to exceed the PDI threshold may represent that fusion-based behavior has occurred.

The value of the Dmax parameter 518 also may indicate whether capture of the stimulus pulse occurred. For example, if the value of the Dmax parameter 518 exceeds a predetermined Dmax threshold, then the value of the Dmax parameter 518 may indicate that capture of the stimulus pulse applied at 416 has occurred. Additionally, if the value of the Dmax parameter 518 exceeds the Dmax threshold, then the value of the Dmax parameter 518 indicates that fusion-based behavior may be present in the heart 102 (shown in FIG. 1). On the other hand, if the value of the Dmax parameter 518 does not exceed the Dmax threshold, then the value of the Dmax parameter 518 may not indicate that capture or fusion-based behavior has occurred.

In one embodiment, if the PDI 514 does not exceed the PDI threshold and value of the Dmax parameter 518 exceeds the Dmax threshold, then the IMD 100 (shown in FIG. 1) determines that fusion-based behavior of the heart 102 (shown in FIG. 1) occurred at 418. If the PDI 514 exceeds the PDI threshold, then the IMD 100 determines at 418 that the heart 102 is not exhibiting fusion-based behavior. Alternatively, if the PDI 514 does not exceed the PDI threshold and the value of the Dmax parameter 518 does not exceed the Dmax threshold, then fusion-based behavior is not detected at 418.

In another embodiment, the IMD 100 (shown in FIG. 1) examines a positive deflection time delay 524 to determine if the heart 102 (shown in FIG. 1) is demonstrating fusion-based behavior. The positive deflection time delay 524 represents the time delay before the positive-sloped portion 520 of the evoked response waveform 508 begins. The positive deflection time delay 524 may be measured as the time period extending between a zero crossing time point 526 and a beginning time point 528 of the positive-sloped section 520 of the evoked response waveform 508. The zero crossing time point 526 represents the time at which the cardiac signal 500 falls below the baseline 516 after application of the stimulus pulse. For example, the zero crossing time point 526 may be the time at which the cardiac signal 500 decreases below zero or crosses the horizontal axis 502 after the paced event 506. The beginning time point 528 represents the time at which the cardiac signal 500 begins to increase from the low point 522 of the negative portion 510 of the evoked response waveform 508. For example, the beginning time point 528 may be the time at which the positive-sloped portion 520 of the evoked response waveform 508 begins.

The length of the positive deflection time delay 524 may be indicative of whether the heart 102 (shown in FIG. 1) is exhibiting fusion-based behavior. In one embodiment, fusion-based behavior of the heart 102 may cause the positive deflection time delay 524 to decrease, or cause the positive-sloped portion 520 of the evoked response 508 to occur earlier after application of a stimulus pulse. The positive deflection time delay 524 may be compared to a predetermined time delay threshold. If the positive deflection time delay 524 exceeds the time delay threshold, then the positive deflection time delay 524 may indicate the presence of fusion-based behavior in the heart 102. Conversely, if the positive deflection time delay 524 does not exceed the time delay threshold, then the positive deflection time delay 524 may not indicate the presence of fusion-based behavior. The IMD 100 (shown in FIG. 1) may compare the positive deflection time delay 524 to the time delay threshold at 418 to determine whether fusion-based behavior of the heart 102 is present.

The above techniques and processes for detecting presence of fusion-based behavior of the heart 102 (shown in FIG. 1) are intended as non-limiting examples. Alternative techniques and processes may be used to detect fusion-based behavior. Additionally, multiple techniques and processes may be combined to identify presence of fusion-based behavior.

Returning to the method 400 of FIG. 3, at 418, if fusion-based behavior of the heart 102 is identified in the cardiac signals, then the fusion-based behavior may indicate that the escape interval 216 (shown in FIG. 2) may need to be adjusted. For example, the escape interval 216 may be modified to avoid or reduce the occurrence of fusion-based behavior in future cardiac cycles. As a result, flow of the method 400 continues to 420. On the other hand, if fusion-based behavior of the heart 102 is not identified in the cardiac signals, then flow of the method 400 continues to 422.

At 420, a modified escape interval is determined when fusion-based behavior of the heart 102 (shown in FIG. 1) is identified at 418. As described below, the modified escape interval is used to adjust the escape interval 216 (shown in FIG. 2) being employed by the IMD 100 (shown in FIG. 1) to determine a new escape interval (and by implication, when to apply stimulus pulses to the heart 102) in subsequent cardiac cycles. The modified escape interval is a modified value of the escape interval 216 that compensates for the detection of fusion-based behavior to avoid or reduce fusion-based behavior in subsequent cardiac cycles. In one embodiment, the modified escape interval represents an escape interval 216 that would have resulted in the stimulus pulse delivered at 416 to be supplied to the heart 102 prior to intrinsic contraction of the heart 102. For example, had the IMD 100 used the modified escape interval at 410 to determine when to supply the stimulus pulses to the ventricles of the heart 102 at 416, the stimulus pulse would have been delivered to the ventricles prior to intrinsic ventricular contraction and would have avoided fusion or pseudo-fusion between the stimulus pulses and the intrinsic ventricular contractions.

In one embodiment, the modified escape interval is a relation of the escape interval 216 (shown in FIG. 2). For example, the modified escape interval is the escape interval 216 lengthened by the time detected for the onset of fusion-based behavior and shortened by one or more of the time between application of stimulus pulses in different chambers of the heart 102 and the paced depolarization time 230 (shown in FIG. 2). The modified escape interval may be represented by the following relationship:

$$MEI = EI + FD - ICPD - PCT \quad \text{(Eqn. 1)}$$

where MEI is the modified escape interval, EI is the escape interval currently being used by the IMD 100 (such as the escape interval 216 or 334), FD represents a fusion delay, ICPD is the interchamber paced delay 222 (shown in FIG. 2), and PCT is the paced depolarization time 230 (shown in FIG. 2). The fusion delay may be a predetermined time period that represents a potential time delay between application of a stimulus pulse and detection of a paced waveform. In one embodiment, the fusion delay used in Equation #1 is between approximately 10 and 40 milliseconds. Alternatively, the fusion delay may be between 10 and 20 milliseconds, although a different time period may be used. By way of example only, if the escape interval 216 is 680 milliseconds, the fusion delay is 35 milliseconds, the interchamber paced delay 222 is 20 milliseconds and the paced depolarization time 230 is 70 milliseconds, using Equation #1, the modified escape interval becomes 680 ms+35 ms−20 ms−70 ms=625 milliseconds. Alternatively, the modified escape interval may be not based on the interchamber paced delay 222. For example, the interchamber paced delay 222 may be dropped from Equation #1 and the modified escape interval may be the escape interval 216 lengthened by the fusion delay and shortened by the paced depolarization time 230.

At 422, the escape interval 216 (shown in FIG. 2) is adjusted based on the modified escape interval. For example, the escape interval 216 that is used by the IMD 100 (shown in FIG. 1) at 410 to determine whether to apply one or more stimulus pulses to the heart 102 (shown in FIG. 1) is adjusted based on the modified escape interval.

In one embodiment, the escape interval 216 is adjusted based on a history of modified escape intervals. The history includes a set of previously determined modified escape intervals and the modified escape interval that is obtained at 420, 432, and 430. The number of modified escape intervals in the history may be manually programmable by an operator or physician of the IMD 100. By way of example only, the history may include 4, 8 or 16 modified escape intervals. The history is dynamically updated as additional modified escape intervals are determined or calculated. For example, the method 400 may operate in a loop-wise manner and determine several modified escape intervals over time. As new modified escape intervals are obtained, the new modified escape intervals are included in the history to replace older, previously determined modified escape intervals. In one embodiment, the history is a first-in, first out database that replaces the oldest modified escape interval with the most recently determined modified escape interval.

Alternatively, the number of modified escape intervals in the history may be based on a calculated pacing percentage. For example, the number of modified escape intervals that are included in the history may be based on the percentage of bi-ventricular pacing that is described in U.S. Pat. No. 7,187, 972, entitled "Bi-Ventricular Pacing In The Face Of Rapidly Conducting Atrial Tachyarrhythmia" (the "'972 patent") In this example, the pacing percentage is based on a ratio of bi-ventricular paced beats to the sum of bi-ventricular paced beats and intrinsic ventricular beats. A modified escape interval that is based on a paced beat may be included in the calculation of the pacing percentage described in the '972 patent as a sensed, intrinsic beat. In another embodiment, a modified escape interval that is based on the detection of fusion-based behavior may be treated as a sensed, intrinsic beat by the '972 patent in the calculation of a pacing percentage.

In one embodiment, the escape interval 216 (shown in FIG. 2) is adjusted based on a statistical function of the modified escape intervals stored in the history. By way of example only, the escape interval 216 may be adjusted by setting the value of the escape interval 216 to be an average, median, deviation, and the like, of the modified escape intervals in the history. Alternatively, the history does not include the longest and shortest modified escape intervals. For example, the escape interval 216 may be modified based on a statistical function of the modified escape intervals in the history except for the highest and lowest modified escape intervals. Once the escape interval 216 is adjusted at 422, flow of the method 400 returns to 408 where additional cardiac signals of the heart 102 (shown in FIG. 1) are monitored by the IMD 100 (shown in FIG. 1).

The method 400 continues to monitor the cardiac signals and determine whether to pace the heart 102 by using the escape interval 216 (shown in FIG. 2) that was adjusted at 422. For example, the escape interval 216 may have been shortened at 422 from a previous value of the escape interval in order to increase the stimulation rate of the IMD 100. Shortening the escape interval 216 when fusion-based behavior is identified may cause the IMD 100 to deliver pacing stimulus pulses sooner after a cardiac event is detected by the IMD 100 at 410 and 416, as described above. Delivering the stimulus paces sooner after detecting cardiac events may result in the stimulus pulses preempting intrinsic cardiac events of the heart 102. For example, shortening the escape interval 216 may cause stimulus pulses to be applied to the ventricles before intrinsic ventricular contraction occurs. Applying the stimulus pulses prior to intrinsic contraction may reduce or avoid the occurrence of fusion-based behavior in the heart 102.

Returning to the operations described in connection with 418, if fusion-based behavior is not detected in connection with the stimulus pulse applied at 416, then flow of the method 400 continues to 432. At 432, a modified escape interval is determined. The modified escape interval is based on the event interval 234 (shown in FIG. 2) between the previously sensed cardiac event and the application of the stimulus pulse at 416. For example, the modified escape interval may be set to the time period between the previous sensed ventricular contraction and the stimulus pulse at 416. At 422, the escape interval 216 (shown in FIG. 2) is adjusted. The modified escape interval determined at 432 is included in the history of modified escape intervals and the escape interval 216 is adjusted, as described above. Flow of the method 400 then continues to 408.

Returning to the operations described above in connection with 410, after sensing an intrinsic cardiac event, the IMD 100 continues to monitor the cardiac signals to determine if the escape interval 216 (shown in FIG. 2) lapses without sensing an additional intrinsic cardiac event, as described above. In contrast to the discussion above, if the IMD 100 does sense an intrinsic cardiac event, such as an intrinsic ventricular contraction, within the escape interval 216 following a previous cardiac event, flow of the method 400 continues along the sensed event path 414.

In the sensed event path 414, at 424, the time period elapsing between the previous cardiac event and the cardiac event sensed at 410 is determined. For example, the IMD 100 (shown in FIG. 1) may measure the event interval 232 (shown in FIG. 2) between the previous intrinsic or paced ventricular contraction and the intrinsic ventricular contraction that was sensed at 410. At 426, the event interval 232 is compared to a predetermined minimum interval. The predetermined minimum interval represents the minimum period of time established by an operator of the IMD 100 or physician. For example, a physician may preset the predetermined minimum interval as the shortest escape interval 216 (shown in FIG. 2) that the physician determines is appropriate for pacing. By way of example only, the predetermined minimum interval may be 500 milliseconds. The predetermined minimum interval may be the shortest period of time that could be used as the escape interval 216.

If the event interval 232 (shown in FIG. 2) measured at 424 is less than the predetermined minimum interval, then the event interval 232 may be too short of a time period to be used to adjust the escape interval 216 (shown in FIG. 2), as described below. For example, if the event interval 232 is shorter than the minimum interval deemed appropriate for use as the escape interval 216 by a physician or operator of the IMD 100 (shown in FIG. 1), then the IMD 100 may not use the measured event interval 232 to adjust the escape interval 216. As a result, flow of the method 400 proceeds to 428. At 428, the value of a modified escape interval is set to the value of the predetermined minimum interval. For example, in contrast to the manner of determining the modified escape interval in the paced path 412 described above, the modified escape interval is established at 428 to be equal to the predetermined minimum interval. Alternatively, the modified escape interval may be set to another predetermined value.

On the other hand, if, at 426, the event interval 232 (shown in FIG. 2) that was measured at 424 is not less than the predetermined minimum interval, then the event interval 232 may be sufficiently long of a time period to be used to adjust the escape interval 216 (shown in FIG. 2), as described below. For example, the event interval 232 may be longer than the minimum time interval deemed appropriate for use as the escape interval 216 by a physician or operator of the IMD 100 (shown in FIG. 1). As a result, flow of the method 400 continues to 430. At 430, the value of a modified escape interval is set to the value of the event interval 232 (shown in FIG. 2) that was measured at 424.

After the modified escape interval is set to either the predetermined minimum interval at 428 or to the measured event interval at 430, flow of the method 400 continues to 422. As described above, at 422, the escape interval 216 (shown in FIG. 2) is adjusted based on a history of modified escape intervals. The history includes the modified escape interval determined at 428 or 430. In one embodiment, the history of modified escape intervals includes a plurality of the modified escape intervals determined at 420, 428, 430 and/or 432. For example, the history may include modified escape intervals obtained in one or more of the pacing path 412 at 420 and/or 432 and the sensing path 414 at 428 and/or 430. The escape interval 216 may be increased based on the history of modified escape intervals. In one embodiment, if the history is comprised of a relatively large number of modified escape intervals that are based upon paced beats, then the escape interval 216 may be increased in order to lower the pacing rate of the IMD 100 (shown in FIG. 1). By way of example only, if the number of modified escape intervals in the history that are based on paced beats exceeds a predetermined threshold or percentage, then the escape interval 216 may be increased by a predetermined amount in order to lower the pacing rate.

Figure 5:
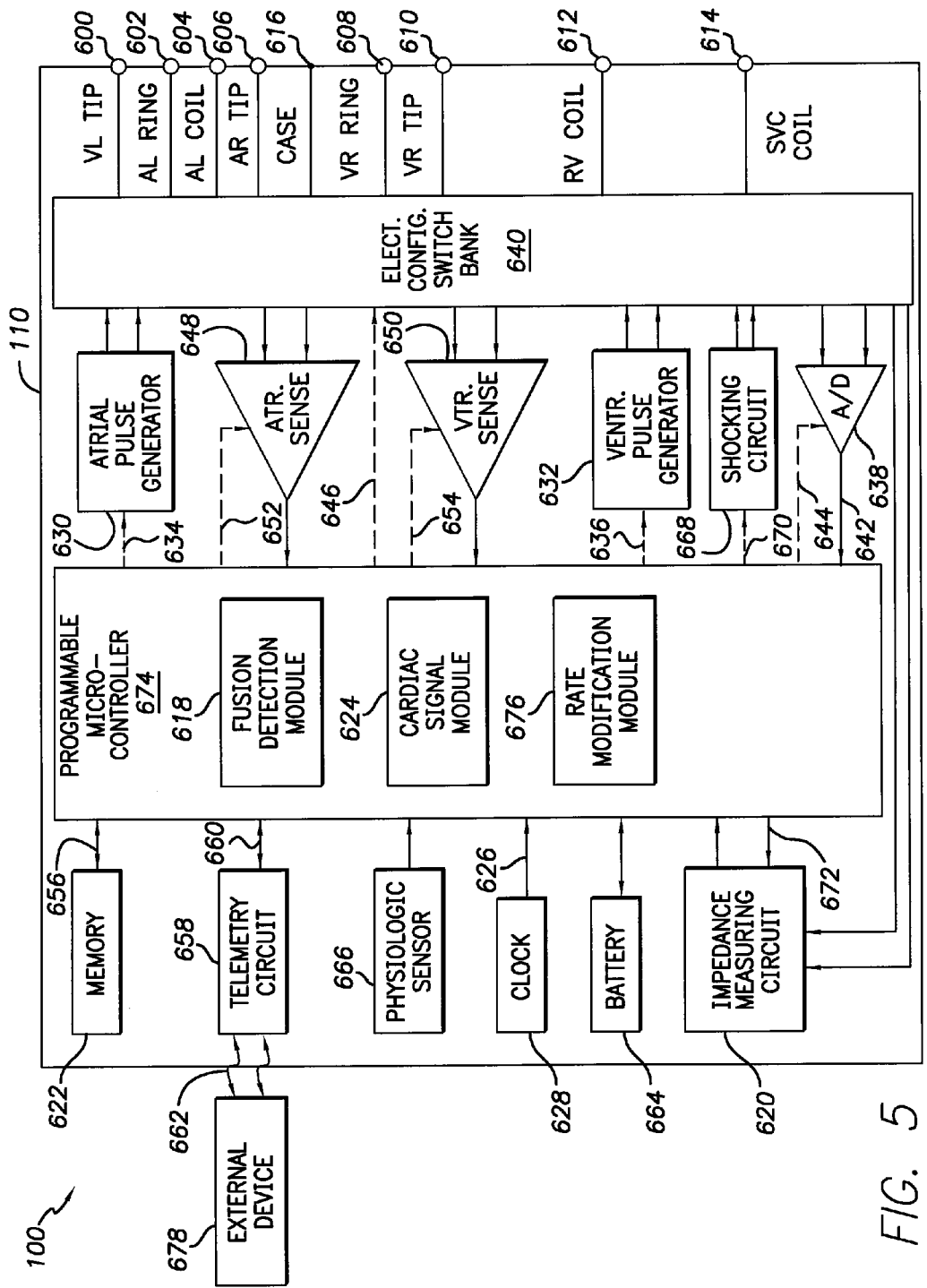
FIG. 5 illustrates a block diagram of exemplary internal components of the IMD shown in FIG. 1.

FIG. 5 illustrates a block diagram of exemplary internal components of the IMD 100. The IMD 100 includes the housing 110. The housing 110 includes several inputs for connecting the electrodes 112-130 (shown in FIG. 1) with the housing 110. The inputs include a left ventricle tip input terminal ($V_L$ TIP) 600, a left atrial ring input terminal ($A_L$ RING) 602, a left atrial coil input terminal ($A_L$ COIL) 604, a right atrial tip input terminal ($A_R$ TIP) 606, a right ventricular ring input terminal ($V_R$ RING) 608, a right ventricular tip input terminal ($V_R$ TIP) 610, an RV coil input terminal 612 and an SVC coil input terminal 614. A case input terminal 616 may be coupled with the housing 110. As their names imply, the input terminals 600-616 may be electrically coupled with the electrodes 112-130.

The IMD 100 includes a programmable microcontroller 674, which controls the operation of the IMD 100. The microcontroller 674 (also referred to herein as a processor, processor module, or unit) typically includes a microprocessor, or equivalent control circuitry, and may be specifically designed for controlling the delivery of stimulation therapy and may further include RAM or ROM memory, logic and timing circuitry, state machine circuitry, and I/O circuitry. For example, the microcontroller 674 may represent a processor or computer specially designed for executing the operations described above in connection with the method 400 (shown in FIG. 3). Among other things, the microcontroller 674 receives, processes, and manages storage of digitized data from the electrodes 112-130 (shown in FIG. 1).

The microcontroller 674 may include one or more modules and processors configured to perform one or more of the actions and determinations described above in connection with the method 400 (shown in FIG. 3). For example, the microcontroller 674 may include a computer software product that is recorded on a computer-readable storage medium, such as a memory 622 or another memory that is internal to the microcontroller 674. The memory 622 or memory that is internal to the microcontroller 674 may be a tangible, solid, real-world machine or device. By way of example only, the memory may include one or more of a ROM, RAM, flash or other type of memory that is used to store information and data readable by a computer processor. The modules described below may be recorded on a computer-readable storage medium such that, when the modules are acted upon by the microcontroller 674 or IMD 100, the functionality described below and in the method 400 may be realized by the IMD 100 or a user of the IMD 100.

The modules of the microcontroller 674 include a fusion detection module 618. The fusion detection module 618 detects the presence of fusion-based behavior in the heart 102 (shown in FIG. 1). For example, the fusion detection module 618 may monitor cardiac signals of the heart 102 to identify the presence of fusion and pseudo-fusion between stimulus pulses applied to the heart 102 and intrinsic cardiac behavior. The fusion detection module 618 may employ one or more of the techniques and processes described above to detect fusion-based behavior. For example, the fusion detection module 618 may obtain the values of the PDI 514 (shown in FIG. 4), the Dmax parameter 518 (shown in FIG. 4), and/or the positive deflection time delay 524 (shown in FIG. 4) to determine if the heart 102 is exhibiting fusion-based behavior.

A cardiac signal module 624 monitors cardiac signals of the heart 102 (shown in FIG. 1) and directs the IMD 100 to deliver one or more stimulus pulses to the heart 102 based on the cardiac signals. For example, the cardiac signal module 624 may monitor the cardiac signals to determine if consecutive cardiac events occur within the escape interval 216 (shown in FIG. 2). As described above, if consecutive cardiac events are not detected over the escape interval 216, or if a subsequent cardiac event occurs outside of the escape interval 216 beginning with the preceding cardiac event, then the cardiac signal module 624 may direct an atrial pulse generator 630 and/or a ventricular pulse generator 632 to supply one or more stimulus pulses to the heart 102. The atrial and ventricular pulse generators 630, 632 are controlled via appropriate control signals 634, 636 to trigger or inhibit the delivery of stimulus pulses to the heart 102. The pulse generators 630, 632 also may provide stimulation pulses to providing a pacing therapy to the patient. The cardiac signal module 624 may measure one or more time periods extending between events represented by the cardiac signals, as described above. By way of example only, the cardiac signal module 624 may measure the event intervals 232, 234 (shown in FIG. 2).

A rate modification module 676 adjusts the stimulation rate at which the stimulus pulses are supplied to the heart 102 (shown in FIG. 1). As described above, the stimulation rate may be modified by shortening the escape interval 216 (shown in FIG. 2) based on the presence of fusion-based behavior. The rate modification module 676 may calculate modified escape intervals and adjustments to the escape interval 216 based thereon. For example, the rate modification module 676 may increase the stimulation rate when fusion-based behavior is detected. The rate modification module 676 communicates the escape interval 216 to the cardiac signal module 624 as the escape interval 216 is adjusted so that the cardiac signal module 624 may determine when to apply stimulus pulses to the heart 102.

The signals sensed by the electrodes 112-130 (shown in FIG. 1) are communicated to the microcontroller 674 via an analog-to-digital (A/D) data acquisition system 638. The cardiac signals obtained by the electrodes 112-130 are applied to the inputs of the data acquisition system 638. The cardiac signals are communicated through the input terminals 600-616 to an electronically configured switch bank 640 before being received by the data acquisition system 638. The data acquisition system 638 converts the raw analog data of the signals obtained by the electrodes 112-130 into digital signals and communicates the signals to the microcontroller 674. A control signal 644 from the microcontroller 674 determines when the data acquisition system 638 acquires signals, stores the signals in a memory 622, or transmits data to an external device 678.

The switch 640 includes a plurality of switches for connecting the desired electrodes 112-130 (shown in FIG. 1) and input terminals 600-616 to the appropriate I/O circuits. The switch 640 closes and opens switches to provide electrically conductive paths between the circuitry of the IMD 100 and the input terminals 600-616 in response to a control signal 646. An atrial sensing circuit 648 and a ventricular sensing circuit 650 may be selectively coupled to the leads 104-108 (shown in FIG. 1) through the switch 640 for detecting the presence of cardiac activity in the chambers of the heart 102 (shown in FIG. 1). Control signals 652, 654 from the microcontroller 674 direct output of the atrial and ventricular sensing circuits 648, 650 that are connected to the microcontroller 674.

The memory 622 may be embodied in a computer-readable storage medium such as a ROM, RAM, flash memory, or other type of memory. The microcontroller 674 is coupled to the memory 622 by a suitable data/address bus 656. The memory 622 may store programmable operating parameters and thresholds used by the microcontroller 674, as required, in order to customize the operation of IMD 102 to suit the needs of a particular patient.

The operating parameters of the IMD 102 may be non-invasively programmed into the memory 622 through a telemetry circuit 658 in communication with the external device 678, such as a trans-telephonic transceiver or a diagnostic system analyzer. The telemetry circuit 658 is activated by the microcontroller 674 by a control signal 660. The telemetry circuit 658 allows information such as, by way of example only, cardiac signals, escape intervals 216 (shown in FIG. 2), contraction times 214 (shown in FIG. 2), interchamber paced delays 222 (shown in FIG. 2), paced depolarization times 230 (shown in FIG. 2), event intervals 232, 234 (shown in FIG. 2) and fusion delays, to be sent to the external device 678 through an established communication link 662.

The IMD 100 includes a battery 664 that provides operating power to the circuits shown within the housing 110, including the microcontroller 674. The IMD 100 also includes a physiologic sensor 666 that may be used to adjust the stimulation rate at which stimulus pulses are applied to the heart 102 (shown in FIG. 1) according to the exercise state of the patient.

An impedance measuring circuit 620 measures impedance vectors between predetermined combinations of the electrodes 112-130 (shown in FIG. 1). The impedance measuring circuit 620 is enabled by the microcontroller 674 via a control signal 672. A clock 628 measures time relative to the cardiac events of the heart 102 (shown in FIG. 1). The clock 628 measures time periods based on start and stop control signals from the microcontroller 674 to monitor paced and intrinsic cardiac events of the heart 102.

In the case where IMD 100 is intended to operate as an ICD device, the IMD 100 detects the occurrence of a shift in one or more waveforms in detected cardiac signals that indicates an arrhythmia, and automatically applies an appropriate electrical shock therapy to the heart aimed at terminating the detected arrhythmia. To this end, the microcontroller 674 further controls a shocking circuit 668 by way of a control signal 670. The shocking circuit 668 generates shocking pulses of low (up to 0.5 joules), moderate (0.5-10 joules) or high energy (11 to 40 joules). Such shocking pulses are applied to the heart 102 (shown in FIG. 1) of the patient through at least two of the electrodes 112-130 (shown in FIG. 1).

Figure 6:
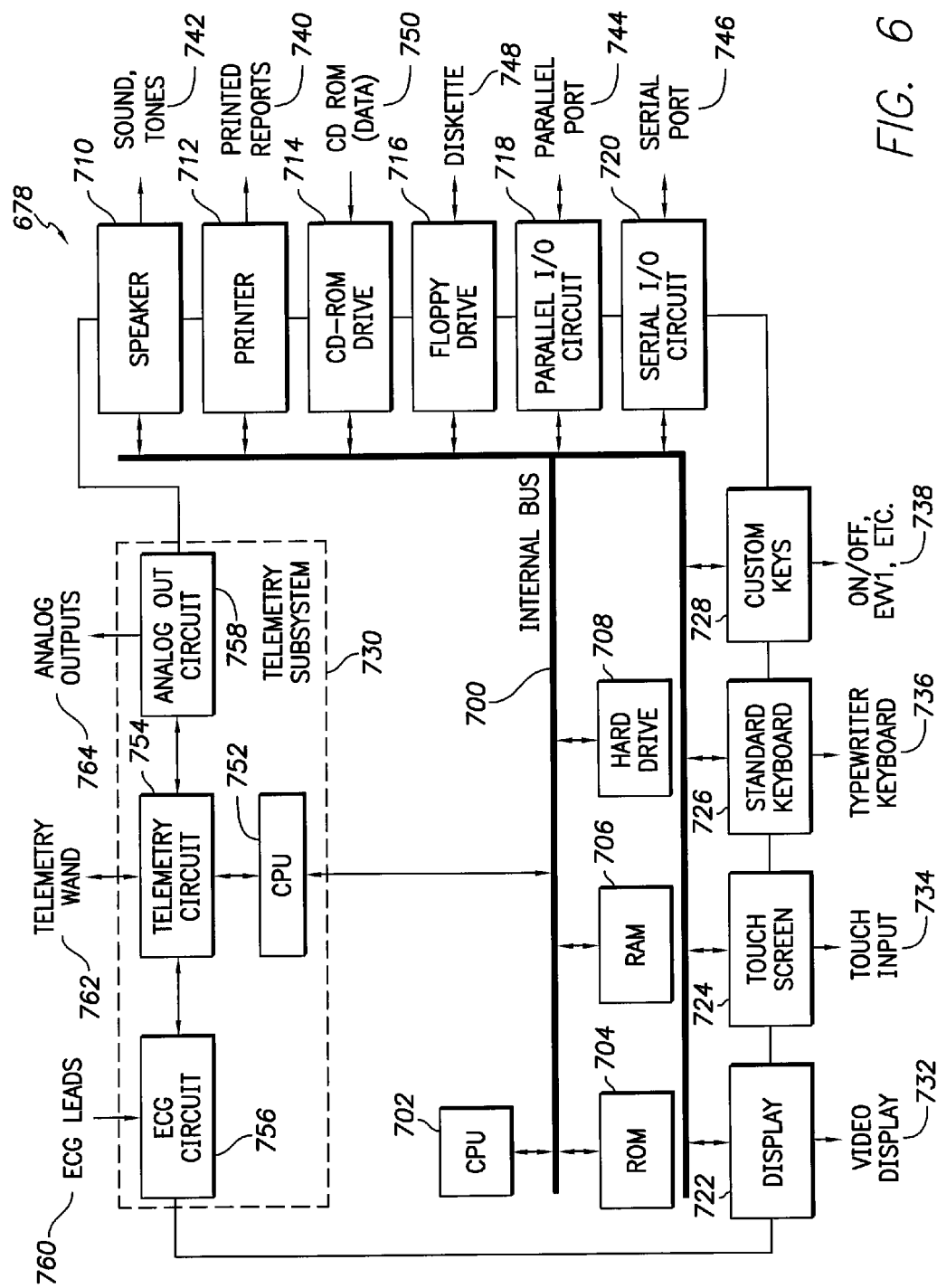
FIG. 6 illustrates a functional block diagram of an external device (shown in FIG. 5) in accordance with one embodiment.

FIG. 6 illustrates a functional block diagram of the external device 678, such as a programmer, that is operated to interface with IMD 100 (shown in FIG. 1). As described above, the external device 678 may be used to communicate and/or program cardiac signals, escape intervals 216 (shown in FIG. 2), contraction times 214 (shown in FIG. 2), interchamber paced delays 222 (shown in FIG. 2), paced depolarization times 230 (shown in FIG. 2), event intervals 232, 234 (shown in FIG. 2) and fusion delays, with the IMD 100. The external device 678 includes an internal bus 700 that connects/interfaces with a Central Processing Unit (CPU) 702, ROM 704, RAM 706, a hard drive 708, the speaker 710, a printer 712, a CD-ROM drive 714, a floppy drive 716, a parallel I/O circuit 718, a serial I/O circuit 720, the display 722, a touch screen 724, a standard keyboard connection 726, custom keys 728, and a telemetry subsystem 730. The internal bus 700 is an address/data bus that transfers information between the various components described herein. The hard drive 708 may store operational programs as well as data, such as escape intervals 216 and the like.

The CPU 702 typically includes a microprocessor, a micro-controller, or equivalent control circuitry, designed specifically to control interfacing with the external device 678 and with the IMD 100 (shown in FIG. 1). The CPU 702 may include RAM or ROM memory 704, logic and timing circuitry, state machine circuitry, and I/O circuitry to interface with the IMD 102. The display 722 (e.g., may be connected to the video display 732) and the touch screen 724 display graphic information relating to the IMD 102. The touch screen 724 accepts a user's touch input 734 when selections are made. The keyboard 726 (e.g., a typewriter keyboard 736) allows the user to enter data to the displayed fields, as well as interface with the telemetry subsystem 730. Furthermore, custom keys 728 turn on/off 738 (e.g., EVVI) the external device 108. The printer 712 prints copies of reports 740 for a physician to review or to be placed in a patient file, and speaker 710 provides an audible warning (e.g., sounds and tones 742) to the user. The parallel I/O circuit 718 interfaces with a parallel port 744. The serial I/O circuit 720 interfaces with a serial port 746. The floppy drive 716 accepts diskettes 748. Optionally, the floppy drive 716 may include a USB port or other interface capable of communicating with a USB device such as a memory stick. The CD-ROM drive 714 accepts CD ROMs 750 or other optical discs.

The telemetry subsystem 730 includes a central processing unit (CPU) 752 in electrical communication with a telemetry circuit 754, which communicates with both an ECG circuit 756 and an analog out circuit 758. The ECG circuit 756 is connected to ECG leads 760. The telemetry circuit 754 is connected to a telemetry wand 762. The analog out circuit 758 includes communication circuits to communicate with analog outputs 764. The external device 678 may wirelessly communicate with the IMD 100 (shown in FIG. 1) and utilize protocols, such as Bluetooth, GSM, infrared wireless LANs, HIPERLAN, 3G, satellite, as well as circuit and packet data protocols, and the like. Alternatively, a hard-wired connection may be used to connect the external device 678 to the IMD 100.

Figure 7:
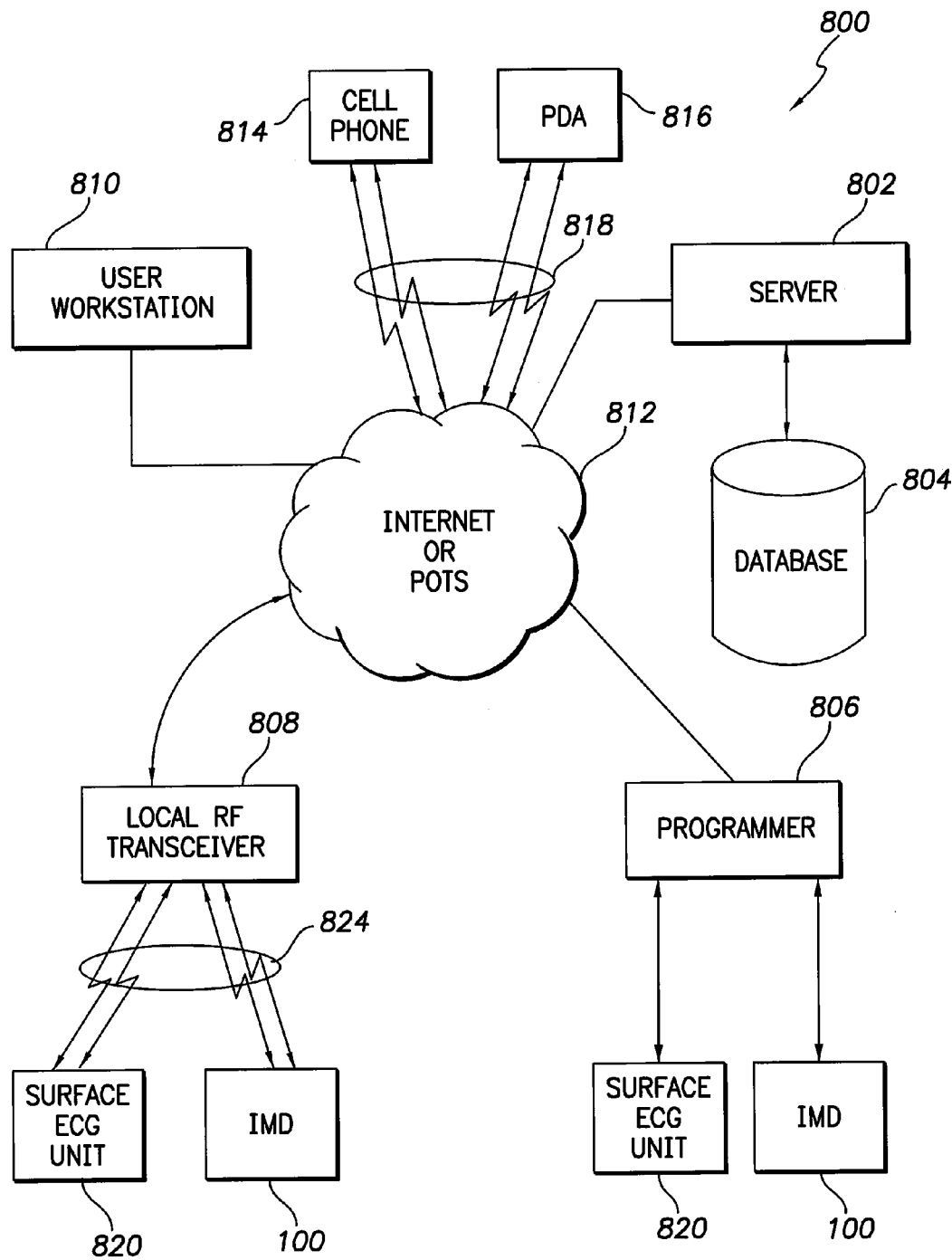
FIG. 7 illustrates a distributed processing system in accordance with one embodiment.

FIG. 7 illustrates a distributed processing system 800 in accordance with one embodiment. The distributed processing system 800 includes a server 802 connected to a database 804, a programmer 806 (e.g., similar to the external device 678 shown in FIG. 5), a local RF transceiver 808 and a user workstation 810 electrically connected to a communication system 812. The communication system 812 may be the internet, a voice over IP (VoIP) gateway, a local plain old telephone service (POTS) such as a public switched telephone network (PSTN), a cellular phone based network, and the like. Alternatively, the communication system 812 may be a local area network (LAN), a campus area network (CAN), a metropolitan area network (MAN), or a wide area network (WAM). The communication system 812 serves to provide a network that facilitates the transfer, receipt, storage and retrieval of information such as cardiac signals, escape intervals 216 (shown in FIG. 2), contraction times 214 (shown in FIG. 2), interchamber paced delays 222 (shown in FIG. 2), paced depolarization times 230 (shown in FIG. 2), event intervals 232, 234 (shown in FIG. 2) and fusion delays.

The server 802 is a computer system that provides services to other computing systems over a computer network. The server 802 interfaces with the communication system 812 to transfer information between the programmer 806, the local RF transceiver 808, the user workstation 810 as well as a cell phone 814, and a personal data assistant (PDA) 816 to the database 804 for storage/retrieval of records of information. On the other hand, the server 802 may upload cardiac signals from a surface ECG unit 820 or the IMD 100 via the local RF transceiver 808 or the programmer 806.

The database 804 stores information such as cardiac signals, escape intervals 216 (shown in FIG. 2), contraction times 214 (shown in FIG. 2), interchamber paced delays 222 (shown in FIG. 2), paced depolarization times 230 (shown in FIG. 2), event intervals 232, 234 (shown in FIG. 2), fusion delays, and the like, for single or multiple patients. The information is downloaded into the database 804 via the server 802 or, alternatively, the information is uploaded to the server from the database 804. The programmer 806 is similar to the external device 678 (shown in FIG. 5) and may reside in a patient's home, a hospital, or a physician's office. Programmer 806 interfaces with the surface ECG unit 820 and the IMD 100. The programmer 806 may wirelessly communicate with the IMD 100 and utilize protocols, such as Bluetooth, GSM, infrared wireless LANs, HIPERLAN, 3G, satellite, as well as circuit and packet data protocols, and the like. Alternatively, a hard-wired connection may be used to connect the programmer 806 to the IMD 100. The programmer 806 is able to acquire cardiac signals from the surface of a person (e.g., ECGs), intra-cardiac electrogram (e.g., IEGM) signals from the IMD 100, and/or cardiac signals, escape intervals 216, contraction times 214, and the like, from the IMD 100. The programmer 806 interfaces with the communication system 812, either via the internet or via POTS, to upload the information acquired from the surface ECG unit 820 or the IMD 100 to the server 802.

The local RF transceiver 808 interfaces with the communication system 812, via a communication link 824, to cardiac signals and the like acquired from the surface ECG unit 820 and/or the IMD 100 to the server 802. In one embodiment, the surface ECG unit 820 and the IMD 100 have a bi-directional connection with the local RF transceiver via a wireless connection. The local RF transceiver 808 is able to acquire cardiac signals from the surface of a person and intra-cardiac electrogram signals from the IMD 100. On the other hand, the local RF transceiver 808 may download stored cardiac signals, escape intervals 216 (shown in FIG. 2), contraction times 214 (shown in FIG. 2), interchamber paced delays 222 (shown in FIG. 2), paced depolarization times 230 (shown in FIG. 2), event intervals 232, 234 (shown in FIG. 2) and fusion delays, and the like, from the database 804 to the surface ECG unit 820 or the IMD 100.

The user workstation 810 may interface with the communication system 812 via the internet or POTS to download data such as cardiac signals, escape intervals 216 (shown in FIG. 2), contraction times 214 (shown in FIG. 2), interchamber paced delays 222 (shown in FIG. 2), paced depolarization times 230 (shown in FIG. 2), event intervals 232, 234 (shown in FIG. 2), fusion delays, and the like, via the server 802 from the database 804. Alternatively, the user workstation 810 may download raw data from the surface ECG unit 820 or IMD 100 via either the programmer 806 or the local RF transceiver 808. The user workstation 810 may download the data to the cell phone 816, the PDA 818, the local RF transceiver 808, the programmer 806, or to the server 802 to be stored on the database 804. For example, the user workstation 810 may communicate the current length of the escape interval 216 to the cell phone 816 of a patient or physician.

Figure 8:
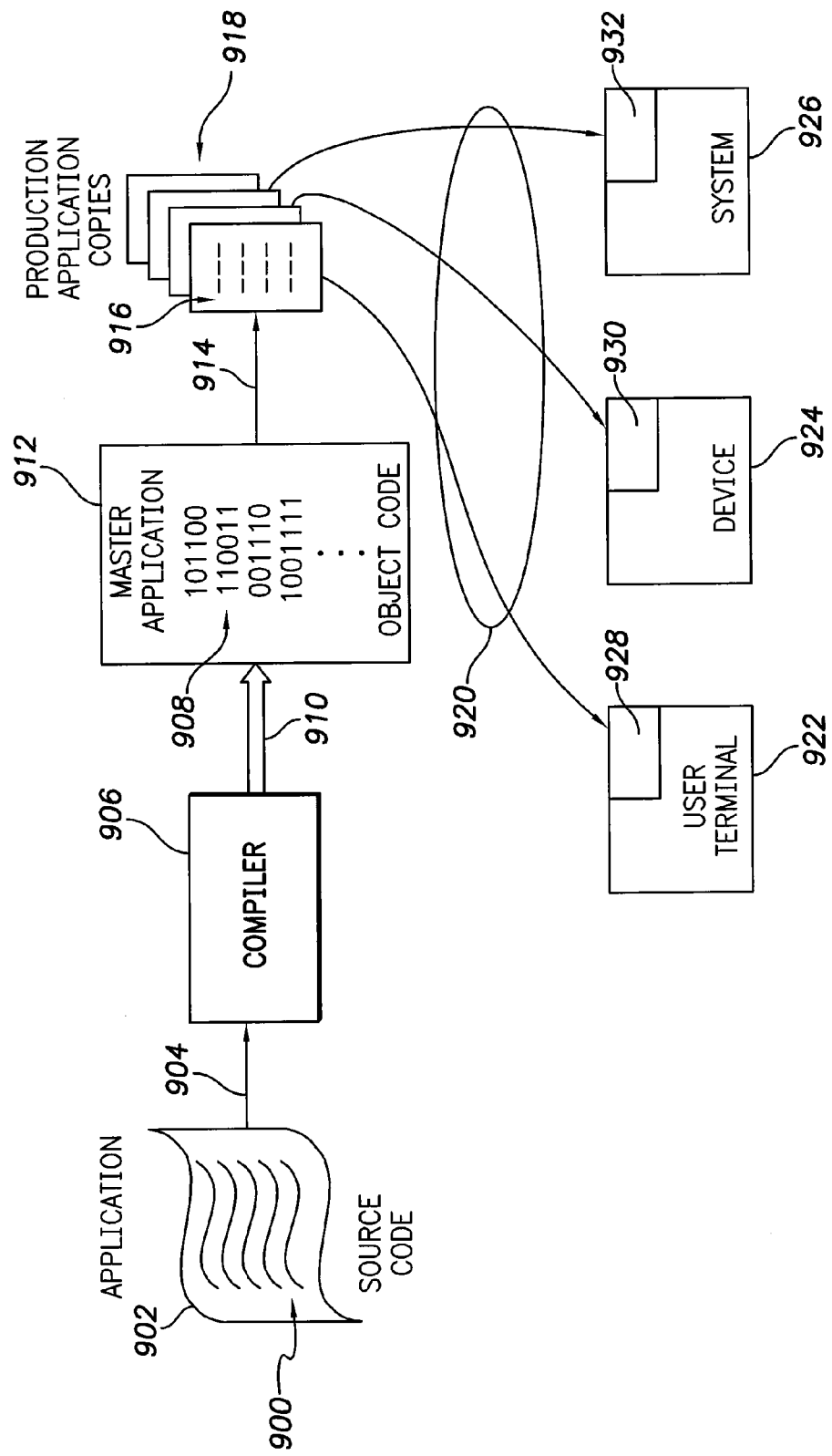
FIG. 8 illustrates a block diagram of example manners in which embodiments of the present invention may be stored, distributed, and installed on a computer-readable medium.

FIG. 8 illustrates a block diagram of exemplary manners in which embodiments of the present invention may be stored, distributed, and installed on a computer-readable medium. In FIG. 8, the "application" represents one or more of the methods and process operations discussed above. The application is initially generated and stored as source code 900 on a source computer-readable medium 902. The source code 900 is then conveyed over path 904 and processed by a compiler 906 to produce object code 908. The object code 908 is conveyed over path 910 and saved as one or more application masters on a master computer-readable medium 912. The object code 908 is then copied numerous times, as denoted by path 914, to produce production application copies 916 that are saved on separate production computer-readable medium 918. The production computer-readable medium 918 is then conveyed, as denoted by path 920, to various systems, devices, terminals and the like.

A user terminal 922, a device 924 and a system 926 are shown as examples of hardware components, on which the production computer-readable medium 918 are installed as applications (as denoted by 928 through 932). For example, the production computer-readable medium 918 may be installed on the IMD 100 (shown in FIG. 1) and/or the microcontroller 674 (shown in FIG. 5). Examples of the source, master, and production computer-readable medium 902, 912, and 918 include, but are not limited to, CDROM, RAM, ROM, Flash memory, RAID drives, memory on a computer system, and the like. Examples of the paths 904, 910, 914, and 920 include, but are not limited to, network paths, the internet, Bluetooth, GSM, infrared wireless LANs, HIPERLAN, 3G, satellite, and the like. The paths 904, 910, 914, and 920 may also represent public or private carrier services that transport one or more physical copies of the source, master, or production computer-readable medium 902, 912 or 918 between two geographic locations. The paths 904, 910, 914 and 920 may represent threads carried out by one or more processors in parallel. For example, one computer may hold the source code 900, compiler 906 and object code 908. Multiple computers may operate in parallel to produce the production application copies 916. The paths 904, 910, 914, and 920 may be intra-state, inter-state, intra-country, inter-country, intra-continental, inter-continental, and the like.

The operations noted in FIG. 8 may be performed in a widely distributed manner world-wide with only a portion thereof being performed in the United States. For example, the application source code 900 may be written in the United States and saved on a source computer-readable medium 902 in the United States, but transported to another country (corresponding to path 904) before compiling, copying and installation. Alternatively, the application source code 900 may be written in or outside of the United States, compiled at a compiler 906 located in the United States and saved on a master computer-readable medium 912 in the United States, but the object code 908 transported to another country (corresponding to path 914) before copying and installation. Alternatively, the application source code 900 and object code 908 may be produced in or outside of the United States, but production application copies 916 produced in or conveyed to the United States (for example, as part of a staging operation) before the production application copies 916 are installed on user terminals 922, devices 924, and/or systems 926 located in or outside the United States as applications 928 through 932.

As used throughout the specification and claims, the phrases "computer-readable medium" and "instructions configured to" shall refer to any one or all of (i) the source computer-readable medium 902 and source code 900, (ii) the master computer-readable medium and object code 908, (iii) the production computer-readable medium 918 and production application copies 916 and/or (iv) the applications 928 through 932 saved in memory in the terminal 922, device 924, and system 926.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An implantable medical device comprising:
   a lead including electrodes configured to be positioned within a heart to sense cardiac signals of the heart;
   a detector to analyze the cardiac signals of the heart and detect atrial arrhythmias;
   a pulse generator electrically coupled to the lead and adapted to deliver stimulus pulses to the heart through at least one of the electrodes;
   a cardiac signal module to monitor the cardiac signals and direct the pulse generator to deliver one or more of the stimulus pulses to the heart at a stimulation rate based on the cardiac signals during a detected atrial arrhythmia;
   a fusion detection module to identify a presence of fusion-based behavior of the heart that is associated with delivery of the one or more of the stimulus pulses during the detected atrial arrhythmia; and
   a rate modification module to adjust the stimulation rate based on the presence of the fusion-based behavior.

2. The implantable medical device of claim 1 wherein the rate modification module increases the stimulation rate when the presence of fusion-based behavior is identified in the heart.

3. The implantable medical device of claim 1, wherein the cardiac signal module determines if consecutive cardiac events occur within an escape interval.

4. The implantable medical device of claim 3, wherein each of the consecutive cardiac events includes at least one of an intrinsic contraction and a paced contraction of one or more chambers of the heart.

5. The implantable medical device of claim 3 wherein the rate modification module adjusts the stimulation rate by modifying the escape interval.

6. The implantable medical device of claim 1 wherein the rate modification module adjusts the stimulation rate based on an event interval extending between delivery of the one or more of the stimulus pulses and identification of the fusion-based behavior.

7. The implantable medical device of claim 1 wherein the rate modification module adjusts the stimulation rate based on a paced contraction time of the heart.

8. The implantable medical device of claim 1, wherein the cardiac signal module measures an event interval elapsing between consecutive cardiac events and wherein the rate modification module adjusts the stimulation rate based on the event interval.

9. The implantable medical device of claim 8, wherein the rate modification module compares the event interval to a predetermined minimum interval and adjusts the stimulation rate based on the predetermined minimum interval when the predetermined minimum interval exceeds the event interval.

10. A method for adjusting a stimulation rate at which an implantable medical device applies stimulus pulses to a heart during an atrial arrhythmia, the method comprising:
    monitoring cardiac signals of the heart;
    analyzing the cardiac signals to detect the atrial arrhythmia;
    delivering one or more stimulus pulses to the heart during the atrial arrhythmia at the stimulation rate based on the cardiac signals;

identifying a presence of fusion-based behavior of the heart that is associated with delivery of the one or more of the stimulus pulses during the atrial arrhythmia; and adjusting the stimulation rate based on the presence of the fusion-based behavior.

11. The method of claim 10, wherein the adjusting operation comprises increasing the stimulation rate when the presence of fusion-based behavior is identified in the heart.

12. The method of claim 10, wherein the monitoring operation comprises determining if consecutive cardiac events occur within an escape interval.

13. The method of claim 12, wherein each of the consecutive cardiac events includes at least one of an intrinsic contraction and a paced contraction of one or more chambers of the heart.

14. The method of claim 12, wherein the adjusting operation comprises modifying the stimulation rate by adjusting the escape interval.

15. The method of claim 12, wherein the delivering operation comprises delivering the one or more of the stimulus pulses to the heart when the consecutive cardiac events occur outside of the escape interval.

16. The method of claim 10, wherein the adjusting operation comprises modifying the stimulation rate based on an event interval extending between delivery of the one or more of the stimulus pulses and identification of the fusion-based behavior.

17. The method of claim 10, wherein the monitoring operation comprises measuring an event interval elapsing between consecutive cardiac events, further wherein the adjusting operation comprises modifying the stimulation rate based on the event interval.

18. The method of claim 17, wherein the adjusting operation comprises comparing the event interval to a predetermined minimum interval and modifying the stimulation rate based on the predetermined minimum interval when the predetermined minimum interval exceeds the event interval.

19. The method of claim 10, wherein the adjusting operation comprises modifying the stimulation rate based on the presence of the fusion-based behavior during an atrial arrhythmia.

20. A computer readable storage medium for use in an implantable medical device having a lead including electrodes configured to be positioned within a heart, a pulse generator configured to deliver stimulus pulses to the heart, and a microcontroller, the computer readable storage medium comprising instructions to direct the microcontroller to:

monitor cardiac signals of the heart using one or more of the electrodes;

detect atrial arrhythmias from the cardiac signals;

instruct the pulse generator to deliver one or more stimulus pulses to the heart at a stimulation rate using at least one of the electrodes when consecutive cardiac events occur outside of an escape interval during the atrial arrhythmia;

identify a presence of fusion-based behavior of the heart that is associated with delivery of the one or more of the stimulus pulses; and adjust the stimulation rate based on the presence of the fusion-based behavior.

* * * * *